(12) United States Patent
Shahid

(10) Patent No.: US 6,342,648 B1
(45) Date of Patent: Jan. 29, 2002

(54) METHODS AND COMPOSITIONS FOR INHIBITING VINYL AROMATIC MONOMER POLYMERIZATION

(75) Inventor: Muslim D. Shahid, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/409,481

(22) Filed: Sep. 30, 1999

(51) Int. Cl.$^7$ .............................. C07C 7/20; B01D 3/34; C09K 15/18
(52) U.S. Cl. .............................. 585/5; 585/4; 585/860; 203/9; 252/182.29; 252/183.12; 252/403; 252/404
(58) Field of Search .............................. 252/183.12, 404, 252/182.18, 182.29, 403; 203/9; 585/5, 860, 4

(56) References Cited

U.S. PATENT DOCUMENTS

| | | | |
|---|---|---|---|
| 4,376,678 A | 3/1983 | Partos | 203/9 |
| 4,774,374 A | 9/1988 | Abruscato et al. | 252/401 |
| 4,929,778 A | 5/1990 | Roling | 252/403 |
| 5,470,440 A | 11/1995 | Arhancet | 252/183.12 |
| 5,562,863 A | 10/1996 | Arhancet | 252/405 |
| 5,773,674 A | * 6/1998 | Arhancet et al. | 252/404 |
| 5,856,542 A | * 1/1999 | Bernhardt et al. | 556/401 |
| 6,025,515 A | * 2/2000 | Shahid | 558/305 |

FOREIGN PATENT DOCUMENTS

WO    WO 98/02403    1/1998

* cited by examiner

*Primary Examiner*—Daniel S. Metzmaier
(74) *Attorney, Agent, or Firm*—Madan, Mossman & Sriram P.C.

(57) ABSTRACT

The present invention provides compositions and methods inhibiting polymerization of vinyl aromatic compounds comprising a bisphenol compound and an oxidized p-phenylenediamine. In a specific, non-limiting embodiment, the polymerization of the vinyl aromatic compound styrene is inhibited by a composition comprising the bisphenol compound 4,4'-methylenebis(2,6-di-tert-butyphenol) and the oxidized p-phenylenediamine compound N-phenyl-N'-methyl-benzoquinonediimide.

16 Claims, No Drawings

METHODS AND COMPOSITIONS FOR INHIBITING VINYL AROMATIC MONOMER POLYMERIZATION

FIELD OF THE INVENTION

This invention relates generally to methods and compositions for inhibiting styrene monomer polymerization.

BACKGROUND OF THE INVENTION

It is well known that undesirable and costly polymerization is a significant problem during the manufacturing of various vinyl monomers, particularly vinyl aromatic compounds (e.g., styrene, alpha-methylstyrene and vinyltoluene). Many kinds of polymerization inhibitors have been used in the past to minimize this problem. For instance, inhibitors such as diethylhydroxylamine, phenyl-p-phenylenediamines, tert-butyl catechol, and phenothiazine have been used to control polymer formation.

During the early 1980s, compounds selected from the groups called alkyl-substituted di-nitro-phenols and nitroso-phenols found widespread use in the styrene industry. However, undesired polymerization, especially during monomer purification processes such as distillation, results in loss of the monomer product. Moreover, loss of production due to polymer formation on process equipment continues to cause operating problems for those in the industry. In particular, plugging of distillation column overhead piping and fouling or plugging of condensers has been problematic. Therefore, the industry has sought compositions and methods that are less dangerous to handle, that are effective in multiple phases, and that reduce product losses and production problems.

SUMMARY OF THE INVENTION

The present invention provides compositions and methods for inhibiting polymerization of vinyl aromatic monomer. The present inventor has discovered that a composition comprising a bisphenol compound and an oxidized p-phenylenediamine compound may effectively inhibit the undesirable and costly polymerization of vinyl aromatic monomer.

DETAILED DESCRIPTION OF THE INVENTION

The present invention relates to compositions and methods for inhibiting polymerization of vinyl aromatic monomer. In one aspect, this invention is directed to a polymerization inhibitor, which may comprise a bisphenol compound and an oxidized p-phenylenediamine compound. The bisphenol and oxidized p-phenylenediamine compound preferably have from about a 1:1 to about a 2:1 molar ratio.

A preferred embodiment of the present invention may comprise a compound of the formula:

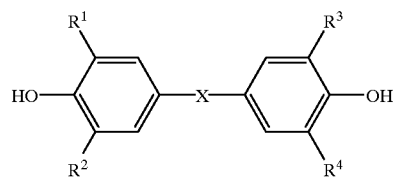

wherein $R^1$, $R^2$, $R^3$, $R^4$ are alkyl groups which may be the same or different;

$X=(CH_2)_n$ wherein n averages from about 1 to about 9; or $X=O$; or $X=S$.

When $X=(CH_2)_n$, n preferably averages from about 1 to about 4. More preferably, X is methylene.

Other preferred bisphenols may have at least one isobutyl alkyl or one tert-butyl alkyl group selected for $R^1$, $R^2$, $R^3$ or $R^4$. More preferably, all four alkyl groups are tert-butyl. Examples of specific bisphenol compounds that would be suitable in the composition of this invention includes, but are not necessarily limited to 4,4'-methylenebis(2,6-di-tert-butylphenol); 2,2'-methylenebis(4-methyl-6-t-butylphenol); 2,2'-methylenebis-6-(1-methylcyclo-hexyl)-p-cresol; and 2,2'-methylenebis(4-methyl-6-cyclohexylphenol).

Another preferred embodiment of the inventive composition may use a benzamine oxidized p-phenylenediamine as the oxidized p-phenylenediamine compound. Preferably, the oxidized p-phenylenediamine compound may comprise benzoquinonediimide. Preferred embodiments of the benzoquinonediimide may selected from the group consisting of N-phenyl-N'-methyl-benzoquinonediimide, N-phenyl-N'-n-hexyl-benzoquinonediimide, N-phenyl-N'-isobutyl-benzoquinonediimide, and N-[4-[(1,3-dimethylbutyl)imino]-2-5-cyclohexadiene-1-ylidene], or mixtures thereof.

A further feature of the present invention may include dispersing the bisphenol and oxidized p-phenylenediamine compounds in a suitable liquid carrier dispersing medium or solvent. Although the type of liquid carrier dispersing medium used is not critical, preferably a liquid hydrocarbon carrier dispersing medium is utilized. More preferably, a non-polar liquid hydrocarbon carrier dispersing medium is utilized. Preferred non-polar liquid hydrocarbon carrier dispersing media include commercial mixtures of xylene isomers or heavy aromatic naphtha.

The liquid hydrocarbon carrier dispersing medium is also preferably substantially inert with respect to the bisphenol and oxidized p-phenylenediamine compound. A substantially inert carrier dispersing medium obviates the need for excess amounts of the two components to be present in the mixture to offset any undesirable reactions. The amount of liquid hydrocarbon carrier dispersing medium mixed with the two components is not critical, but preferably, solubility limits of the bisphenol and oxidized p-phenylenediamine compounds are not exceeded. More preferably, a sufficient amount of liquid hydrocarbon carrier dispersing medium is used to prevent exceeding solubility limits under the coldest temperatures anticipated for shipment or storage of the inventive composition. This preferred embodiment may avoid precipitation of the bisphenol and oxidized p-phenylenediamine compounds that could result in ineffective dispersion of the polymerization inhibitor.

As previously described, the relative amount of the liquid hydrocarbon carrier dispersing medium in relationship to the inventive composition is not critical. However, the amount may be preferentially varied to facilitate the addition of the invention composition to the monomer phase (e.g., for flow measurement, for pumping, for injection into storage tanks, or for feeding distillation columns).

The composition, in another aspect, may also comprise at least one vinyl aromatic monomer phase (e.g., liquid, vapor or plasma). For example, the composition may be introduced as the vinyl aromatic monomer in the vapor state is being passed through pipes or heat exchange tubes (e.g., in overhead condenser to a distillation column).

One preferred composition could have a bisphenol compound concentration is from about 1 ppm by weight to about 2000 ppm by weight in the at least one vinyl aromatic monomer phase relative to the total weight of vinyl aromatic monomer phase. Also preferably, the oxidized p-phenylenediamine compound may be present in at least one vinyl aromatic monomer phase from about 1 ppm by weight to about 2000 ppm by weight. More preferably, the bisphenol compound concentration and the oxidized p-phenylenediamine concentration in the at least one vinyl aromatic monomer phase is from about 50 ppm by weight to about 500 ppm by weight. Still more preferably, the bisphenol compound concentration and the oxidized p-phenylenediamine concentration in the at least one vinyl aromatic monomer phase is from about 150 ppm by weight to about 300 ppm by weight. Examples of the vinyl aromatic monomer phase that would be suitable in the composition of this invention include, but are not necessarily limited to styrene, alpha-methylstyrene and vinyl-toluene.

The present invention also provides methods for inhibiting the polymerization of vinyl aromatic monomer. The composition may be used as both a process inhibitor, which is employed during the synthesis and processing of the vinyl aromatic monomer and as a product inhibitor, employed during storage, shipping and handling. Thus, use of the inventive method may control the fouling of process equipment, such as that used in synthesis, separation, purification and storage processes.

One embodiment of the present inventive method may comprise the steps of providing at least one vinyl aromatic monomer phase and adding an effective amount of a composition comprising a bisphenol compound and an oxidized p-phenylenediamine compound. Thus, the composition may be introduced into a vapor state or a liquid state. The inventive method may be used with styrene, alpha-methylstyrene and vinyl-toluene monomer phases. A preferred method would use a benzamine oxidized p-phenylenediamine compound as the oxidized p-phenylenediamine. Examples of specific benzamine oxidized p-phenylenediamine compounds that would be suitable for the inventive methods include, but are not necessarily limited to, N-phenyl-N'-methyl-benzoquinonediimide, N-phenyl-N'-n-hexyl-benzoquinonediimide, N-phenyl-N'-isobutyl-benzoquinonediimide and N-[4-[(1,3-dimethylbutyl)imino]-2-5-cyclohexadiene-1-ylidene], or mixtures thereof.

The total amount of the bisphenol compound and the oxidized p-phenylenediamine compound in the composition commonly varies according to the conditions under which the vinyl aromatic monomer is synthesized, processed, and/or stored. The formation of the undesired polymers may be very responsive to temperature, which varies with the processing pressure. At higher temperatures, larger amounts of the composition are generally required. The polymerization may also be responsive to the cleanliness of the equipment. For example, if there is a presence of polymer "seed" in the equipment, the effectiveness of the composition may decrease, requiring a higher concentration of the bisphenol and/or oxidized p-phenylenediamine compound in the vinyl aromatic phase.

In adding the effective amount of the composition to inhibit polymerization of the at least one vinyl aromatic monomer phase, the bisphenol compound and the oxidized p-phenylenediamine compounds are preferably dispersed in a suitable liquid carrier dispersing medium. These compounds may be dispersed into a single carrier and blended into a single mixture. Alternatively, each compound may be separately dispersed into a suitable liquid carrier. When dispersed, the carriers are not required to be of the same chemical make-up. Additionally, if separately dispersed, each compound with its carrier may be added individually to the at least one vinyl aromatic monomer phase provided that each separately compound is added and dispersed in the at least one vinyl aromatic monomer phase in an amount effective to inhibit polymerization of the monomer phase.

One preferred embodiment preferably uses a bisphenol compound in a concentration from about 150 ppm by weight to about 300 ppm by weight relative to the total weight of vinyl aromatic monomer phase. The benzamine oxidized p-phenylenediamine compound concentration may preferably be from about 150 ppm by weight to about 300 ppm by weight in at least one vinyl aromatic monomer phase. A further feature of the inventive method for inhibiting polymerization of vinyl aromatic monomer may comprise the steps of providing at least one vinyl aromatic monomer phase and adding an amount effective to inhibit polymerization of the at least one vinyl aromatic monomer phase of a composition comprising a bisphenol compound and an oxidized p-phenylenediamine compound and dispersing the composition in the at least one vinyl aromatic monomer phase so that the concentration of the composition is from about 50 ppm by weight to about 500 ppm by weight.

Another feature of this aspect of the present invention is dispersing an effective amount of composition in a first vinyl aromatic monomer phase that is liquid and a second vinyl aromatic monomer phase that is vapor. Examples of suitable chemical components comprising the liquid, vapor and/or plasma vinyl aromatic monomer phases may include, but are not necessarily limited to styrene, alpha-methylstyrene and vinyl-toluene. A preferred method of the present invention disperses the composition in distillation equipment.

While preferred embodiments have been shown and described, various modifications and substitutions may be made thereto without departing from the spirit and scope of the invention. Accordingly, it is intended that all variations within the scope and spirit of the appended claims be embraced by the foregoing disclosure.

What is claimed is:

1. A composition for inhibiting polymerization of vinyl aromatic monomer comprising:

(a) the methylene bisphenol compound of 4,4'-methylenebis(2,6-di-tert-butylphenol) and (b) an oxidized p-phenylenediamine compound selected from the group consisting of N-phenyl-N'-methyl-benzoquinonediimide, N-phenyl-N'-hexyl-benzoquinonediimide, N-phenyl-N'-isobutyl-benzoquinonediimide, N-[4-[(1,3-dimethylbutyl)imino]-2-5-cyclohexadien-1-ylidene], and mixtures thereof.

2. The composition of claim 1, wherein the bisphenol compound and the oxidized p-phenylenediamine compound have from about a 1:1 to about a 2:1 molar ratio.

3. The compositions of claim 2, further comprising a hydrocarbon liquid carrier dispersing medium.

4. The composition of claim 1 further comprising a liquid hydrocarbon carrier dispersing medium.

5. A polymerization inhibited vinyl aromatic composition comprising:

(a) the methylene bisphenol compound of 4,4'-methylenebis(2,6-di-tert-butylphenol);

(b) an oxidized p-phenylenediamine compound selected from the group consisting of N-phenyl-N'-methyl-benzoquinonediimide, N-phenyl-N'-hexyl-benzoquinonediimide, N-phenyl-N'-isobutyl-benzoquinonediimide, N-[4-[(1,3-dimethylbutyl)imino]-2-5-cyclohexadien-1-ylidene], and mixtures thereof; and (c) at least one vinyl aromatic monomer phase.

6. The composition of claim 5, wherein the bisphenol compound concentration is from about 1 ppm by weight to about 2000 ppm by weight and wherein the oxidized p-phenylenediamine compound concentration is from about 1 ppm by weight to about 2000 ppm by weight in the at least one vinyl aromatic monomer phase.

7. The composition of claim 5, wherein the bisphenol compound concentration is from about 50 ppm by weight to about 500 ppm by weight and wherein the oxidized p-phenylenediamine compound concentration is from about 50 ppm by weight to about 500 ppm by weight in the at least one vinyl aromatic monomer phase.

8. The composition of claim 5, wherein the bisphenol compound concentration is from about 150 ppm by weight to about 300 ppm by weight and wherein the oxidized p-phenylenediamine compound concentration is from about 150 ppm by weight to about 300 ppm by weight in the at least one vinyl aromatic monomer phase.

9. The composition of claim 5, wherein the at least one vinyl aromatic monomer phase comprises styrene.

10. A method for inhibiting the polymerization of vinyl aromatic monomer comprising:
    providing at least one vinyl aromatic monomer phase; and
    adding thereto a composition in an amount effective to inhibit polymerization of the at least one vinyl aromatic monomer phase, said composition comprising the methylene bisphenol compound of 4,4'-methylenebis (2,6-di-tert-butylphenol) and an oxidized p-phenylenediamine compound selected from the group consisting of N-phenyl-N'-methyl-benzoquinonediimide, N-phenyl-N'-hexyl-benzoquinonediimide, N-phenyl-N'-isobutyl-benzoquinonediimide, N-[4-[(1,3-dimethylbutyl)imino]-2-5-cyclohexadien-1-ylidene], and mixtures thereof.

11. The method of claim 10 wherein the at least one vinyl aromatic monomer phase is selected from the group consisting of styrene, alpha-methylstyrene and vinyl-toluene.

12. The method of claim 10, wherein the bisphenol compound concentration is from about 150 ppm by weight to about 300 ppm by weight and wherein the oxidized p-phenylenediamine compound is from about 150 ppm by weight to about 300 ppm by weight concentration in the at least one vinyl aromatic monomer phase.

13. A method for inhibiting the polymerization of vinyl aromatic monomer comprising:
    providing at least one vinyl aromatic monomer phase; and
    adding thereto a composition in an amount effective to inhibit polymerization of the at least one vinyl aromatic monomer phase, said composition comprising the methylene bisphenol compound of 4,4'-methylenebis (2,6-di-tert-butylphenol) and an oxidized p-phenylenediamine compound selected from the group consisting of N-phenyl-N'-methyl-benzoquinonediimide, N-phenyl-N'-hexyl-benzoquinonediimide, N-phenyl-N'-isobutyl-benzoquinonediimide, N-[4-[(1,3-dimethylbutyl)imino]-2-5-cyclohexadien-1-ylidene], and mixtures thereof; and
    dispersing said effective amount of the composition wherein the composition is from about 50 ppm by weight to about 500 ppm by weight in the at least one vinyl aromatic monomer phase.

14. The method of claim 13, wherein the at least one vinyl aromatic monomer phase comprises a first vinyl aromatic monomer phase as liquid and a second vinyl aromatic monomer phase as vapor.

15. The method of claim 13, wherein the at least one vinyl aromatic monomer phase comprises styrene.

16. The method of claim 13, wherein the dispersing further comprises passing the composition and at least one vinyl monomer phase through distillation equipment.

* * * * *